United States Patent [19]

Ruland et al.

[11] Patent Number: 4,754,044
[45] Date of Patent: Jun. 28, 1988

[54] PREPARATION OF KETENE O,N-ACETALS

[75] Inventors: Alfred Ruland, Hirschberg; Wolfgang Reuther, Heidelberg, both of Fed. Rep. of Germany

[73] Assignee: BASF Aktiengesellschaft, Ludwigshafen, Fed. Rep. of Germany

[21] Appl. No.: 11,383

[22] Filed: Feb. 5, 1987

Related U.S. Application Data

[63] Continuation of Ser. No. 799,205, Nov. 19, 1985, abandoned, which is a continuation of Ser. No. 545,878, Oct. 27, 1983, abandoned.

[30] Foreign Application Priority Data

Oct. 30, 1982 [DE] Fed. Rep. of Germany ....... 3240288

[51] Int. Cl.$^4$ ............... C07D 249/08; C07D 233/60; C07D 231/12; C07D 235/06
[52] U.S. Cl. .................................. 548/262; 548/333; 548/341; 548/378
[58] Field of Search ............... 548/341, 333, 378, 262

[56] References Cited

U.S. PATENT DOCUMENTS

| | | | |
|---|---|---|---|
| 2,883,368 | 4/1959 | Middleton | 260/78.4 |
| 3,531,494 | 9/1970 | Adolphi et al. | 260/309 |
| 3,641,248 | 2/1972 | Adolphi et al. | 424/212 |
| 4,147,791 | 4/1979 | Meiser et al. | 548/262 |
| 4,539,160 | 9/1985 | Ruland et al. | 260/465 |

FOREIGN PATENT DOCUMENTS

| | | | |
|---|---|---|---|
| 56125 | 7/1982 | European Pat. Off. | 548/262 |
| 0071095 | 2/1983 | European Pat. Off. | 548/341 |

OTHER PUBLICATIONS

H. D. Stachel, Chem. Ber., vol. 93 (1960), 1059-1063.
Middleton, Chem. Abstracts, vol. 53, Cal. 18872 (1959).
Borrmann, Houben-Weyls Methoden der Organischen Chemie, vol. 74 (Stuttgart, 1968), pp. 362-364.

*Primary Examiner*—Glennon H. Hollrah
*Assistant Examiner*—Patricia L. Morris
*Attorney, Agent, or Firm*—Keil & Weinkauf

[57] ABSTRACT

Ketene O,N-acetals of the formula I

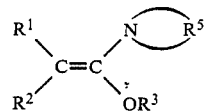

where $R^1$ is tertiary alkyl of 4 to 6 carbon atoms, $R^2$ is hydrogen, $R^3$ is phenyl which is unsubstituted or substituted by halogen, alkoxy, alkyl, phenyl, phenoxy, cyano, nitro or trifluoromethyl and

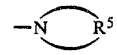

is a triazole, pyrazole, benzimidazole or imidazole radical, are prepared by a process in which a ketene O,O-acetal of the formula II

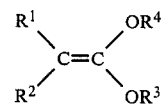

where $R^1$, $R^2$ and $R^3$ have the above meanings and $R^4$ is phenyl which is unsubstituted or substituted by halogen, alkoxy, alkyl, phenyl, phenoxy, cyano, nitro or trifluoromethyl, is reacted with a compound of the formula

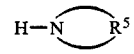

where

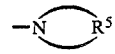

has the above meanings, at elevated temperatures.

4 Claims, No Drawings

PREPARATION OF KETENE O,N-ACETALS

This application is a continuation of application Ser. No. 799,205, filed on Nov. 19, 1985, now abandoned which is a continuation of application Ser. No. 545,878, filed on Oct. 27, 1983, now abandoned.

The present invention relates to a process for the preparation of ketene O,N-acetals by reacting the corresponding ketene O,O-acetals with a heterocyclic nitrogen compound.

Ketene O,N-acetals and their use as fungicides have been disclosed (European Pat. No. 56,125). They are prepared by decomposing the corresponding phenylsulfonates at from 10° to 100° C. in the presence of a solvent and of a catalyst.

This preparation process has the disadvantage that the ketene O,N-acetal is obtained in the form of a mixture of the E and Z isomers. Where only one of the two isomers is of interest, the isomers have to be separated, and the isomer which is not required is inevitably obtained.

We have found that ketene O,N-acetals of the formula I

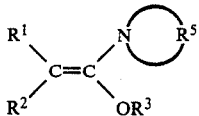
I where $R^1$ is tertiary alkyl of 4 to 6 carbon atoms, $R^2$ is hydrogen, $R^3$ is phenyl which is unsubstituted or substituted by halogen, alkoxy, alkyl, phenyl, phenoxy, cyano, nitro or trifluoromethyl, and

is a triazole, pyrazole, benzimidazole or imidazole radical, are obtained if a ketene O,O-acetal of the formula II

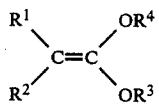
II where $R^1$, $R^2$ and $R^3$ have the above meanings and $R^4$ is phenyl which is unsubstituted or substituted by halogen, $C_1$–$C_2$-alkoxy, $C_1$–$C_4$-alkyl, phenyl, phenoxy, cyano, nitro or trifluoromethyl, is reacted with a compound of the formula

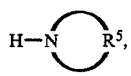

where

has the above meanings, at elevated temperatures.

$R^1$ is, for example, tertiary butyl. $R^3$ is, for example, phenyl which is substituted by halogen (F, Cl or Br), alkoxy of 1 or 2 carbon atoms (methoxy) or alkyl of 1 to 4 carbon atoms (methyl, ethyl, propyl, i-propyl, butyl, sec.-butyl, tert.-butyl or i-butyl), monosubstitution or polysubstitution (disubstitution or trisubstitution) by a particular radical or polysubstitution by different radicals being possible, eg. 4-chlorophenyl, 3,4-dichlorophenyl, 4-chloro-3-bromophenyl or 4-methyl-3-chlorophenyl.

is, for example, 1,2,4-triazol-1-yl or 1,2,3-triazol-1-yl.

Elevated temperatures are, for example, temperatures above 80° C.

In contrast to the conventional process, the novel process gives an E or Z isomer in virtually quantitative yield and with a purity of from 75 to 95%. The substantially pure isomers can be readily purified in a conventional manner (recrystallization or adsorption on an adsorbent) to give the completely pure isomers. Depending on the structure of the starting materials, the reaction gives either the E isomer or the Z isomer. In the case of the conventional process, the phenylsulfonates used as starting materials are in the form of diastereomer mixtures because they contain two asymmetric carbon atoms. In the conventional decomposition of this mixture of diastereomeric phenylsulfonates, a mixture of the E and Z isomers is formed. The conventional processes has the disadvantages that the diastereomer mixtures have to be separated before the decomposition, the separation procedure being involved and difficult in some cases, and that the separation inevitably gives the isomer which is not desired, with the result that the total yield is reduced, in some cases substantially. These disadvantages are also present if separation of the isomers is carried out after the decomposition.

The novel process can be carried out in the presence of a solvent, but it is advantageously carried out in the absence of one; it can be carried out under superatmospheric pressure, but is advantageously carried out under atmospheric pressure. It is essential that the elevated temperatures required for the reaction, preferably 180°–200° C., are reached. In the reaction, the radical —$OR^4$ is converted to the corresponding phenol derivative $HOR^4$. In the course of the reaction, increasing amounts of this phenol derivative are formed. It does not interfere with the reaction, and hence need not be removed continuously from the reaction mixture. When the reaction is complete, the phenol derivative formed can be separated off from the end product or its solution in an organic solvent in a conventional manner, for example by converting the phenol derivative to the corresponding water-soluble alkali metal phenolate.

The reaction can be carried out, for example, with an excess (eg. of up to 10%) of one of the reactants (eg. the compound

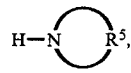

in particular 1,2,3-triazole). Preferably, the starting materials are used in stoichiometric amounts.

The substantially pure isomers obtained as end products of the reaction can be used as fungicides, without further purification being required. The ketene O,O-acetals of the formula II which are required as starting materials are obtained by converting an alpha-hydroxyacetal of the formula III

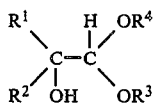

to the corresponding sulfonate, carboxylate, carbonate or dithiocarbonate and separating off the corresponding acid from the resulting ester in the presence of a basic catalyst, in accordance with the following equations:

$$\underset{R^2}{\overset{R^1}{\diagdown}}C-\underset{OR^3}{\overset{H\ \ OR^4}{\diagup}}C + \text{p-toluenesulfonyl chloride} \xrightarrow{\text{(TS—Cl)}}$$

$$\underset{R^2}{\overset{R^1}{\diagdown}}C-\underset{\underset{TS}{\overset{|}{O}}\ \ \ OR^3}{\overset{H\ \ OR^4}{\diagup}}C \xrightarrow{\text{alkali}}$$

$$\underset{R^2}{\overset{R^1}{\diagdown}}C=\underset{OR^3}{\overset{OR^4}{\diagup}}C + \text{alkali metal p-toluenesulfonate}$$

The starting materials can be prepared by the method below.

Method a₁ Tosylation of 1,1-bis-(2,4-dichlorophenoxy)-3,3-dimethylbutan-2-ol 42.4 g (0.1 mole) of 1,1-bis-(2,4-dichlorophenoxy)-3,3-dimethylbutan-2-ol in 200 ml of absolute tetrahydrofuran are reacted with an equimolar amount of a solution of n-butyl-lithium in n-hexane at −10° C. Thereafter, 19.1 g (0.1 mole) of p-toluenesulfonyl chloride are added, the mixture is allowed to thaw by warming up to room temperature (20° C.), stirring is continued for about 1 hour, the solvent is distilled off under reduced pressure and the residue is taken up in ethyl acetate. The organic phase is washed twice with water, dried and evaporated down, and the crude product is recrystalized from cyclohexane/ethyl acetate.

Yield: 51.8 g (95% of theory)

Mp.: 87°–88° C.

¹H-NMR: δ=1.25 (s, 3H); 2.4 (s, 3H); 4.85 (d, 1H); 6.05 (d, 1H); 6.5–7.9 (m, 10H). a₂ Tosylation of 1,1-bis-(4-chlorophenoxy)-3,3-dimethylbutan-2-ol 3 g (0.1 mole) of 80% strength sodium hydride are added to 35.6 g (0.1 mole) of 1,1-bis-(4-chlorophenoxy)-3,3-dimethylbutan-2-ol in 200 ml of absolute tetrahydrofuran, and the mixture is heated at 40° C. As soon as the evolution of gas has ceased, 19.1 g (0.1 mole) of p-toluenesulfonyl chloride are added and stirring is continued for 1 hour at room temperature, after which the mixture is hydrolyzed with a little water and then evaporated down under reduced pressure. The residue is taken up in ethyl acetate, and the solution is washed twice with water, dried and again evaporated down under reduced pressure. The crude product which remains is recrystallized from ethyl acetate/cyclohexane.

Yield: 41.7 g (82% of theory)

Mp.: 97° C.

¹H-NMR: δ=1.25 (s, 9H); 2.3 (s, 3H); 4.8 (d, 1H); 5.8 (d, H); 6.5–7.9 (m, 12H).

The following compounds were prepared by the same method:

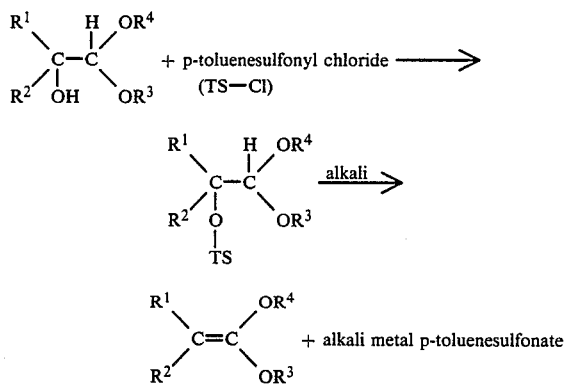

+ = tertiary butyl

| R¹ R² = R³ | M.p. in °C. | H—NMR-data (CDCl₃) |
|---|---|---|
| 2-Cl | 79 | δ = 1.2 (s, 9H); 2.3 (s, 3H); 4.9 (d, 1H); 6.1 (d, 1H); 6.5–7.9 (m, 12H) |
| 4-Br | 93–95 | δ = 1.2 (s, 9H); 2.3 (s, 3H); 4.8 (d, 1H); 5.8 (d, 1H); 6.5–7.9 (m, 12H) |
| 3,5 Cl₂ | 124–126 | δ = 1.2 (s, 9H); 2.4 (s, 3H); 4.85 (d, 1H); 5.8 (d, 1H); 6.6–7.9 (m, 10H); |
| 2,4,5 Cl₃ | 116–118 | δ = 1.2 (s, 9H); 2.35 (s, 3H); 4.85 (s, 1H); 5.95 (s, 1H); 6.8–7.9 (m, 8H) | b₁ 1,1-bis-(2,4-Dichlorophenoxy)-3,3-dimethylbut-1-ene

An equimolar amount of potassium tert.-butylate is added to 54.6 g (0.1 mole) of the tosylate of 1,1-bis-(2,4-dichlorophenoxy)-3,3-dimethylbutan-2-ol in 200 ml of dry dimethylsulfoxide. The mixture is stirred for 30 minutes at room temperature, after which it is hydrolyzed with water and then extracted twice with the same volume of ethyl acetate, the organic phase is dried and the solvent is distilled off under reduced pressure.

Yield: 38.57 g (95% of theory)

Bp.: 175°–176° C./0.5 mbar

¹H-NMR δ=1.2 (s, 9H); 4.85 (s, 1H); 7.73 (m, 6H).

b₂ 1,1-bis-(4-Chlorophenoxy)-3,3-dimethylbut-1-ene 39 g (0.5 mole) of sodium sulfide are added to 47.8 g (0.1 mole) of the tosylate of 1,1-bis-(4-chlorophenoxy)-3,3-dimethylbutan-2-ol in 200 ml of dry dimethylsulfoxide, and the mixture is stirred at 120° C. until starting material is no longer detectable by high pressure liquid chromatography (HPLC). Thereafter, the mixture is cooled, water is added and the mixture is extracted twice with the same volume of ethyl acetate, the organic phase is dried and the solvent is distilled off under reduced pressure.

Yield: 25.3 g (75% of theory)

$^1$H-NMR: δ=1.2 (s, 9H); 4.8 (s, 1H); 6.8–7.4 (m, 8H).

The further Examples below were prepared by the same method:

![structure: R1\C=C/O-phenyl-R2, with H and O-phenyl-R3]

| R$^1$ | R$^2$ = R$^3$ | H—NMR-data (CDCl$_3$) |
|---|---|---|
| + | 2-Cl | δ = 1.2 (s, 9H); 4.8 (s, 1H) 6.8–7.4 (m, 8H) |
| + | 4-Br | δ = 1.15 (s, 9H), 4.8 (s, 1H); 6.7–7.5 (m, 8H) |
| + | 3,5-Cl$_2$ | δ = 1.15 (s, 9H), 4.95 (s, 1H); 6.8–7.1 (m, 6H) |
| + | 2,4,5-Cl$_3$ | δ = 1.2 (s, 9H); 4.95 (s, 1H); 7.25–7.5 (m, 4H) |

Exchange reactions similar to the novel process are known in principle. However, these are virtually exclusively reactions involving activated ketene O,O-acetals. These are ketene O,O-acetals which in the β-position possess electron-attracting substituents, eg. —CHO, —COOR, —SO$_2$, —CN, etc. (cf. for example H.D. Stachel, Vol. 93 (1960), 1059, U.S. Pat. No. 2,883,368 and C.A. 53 (1959), 18872). Furthermore, their reaction with amines always leads to mixtures of ketene O,N-acetals and ketene N,N-acetals, which as a rule are difficult to separate.

It is therefore all the more surprising that ketene O,O-acetals where OR is the phenol radical can be reacted with heterocyclic compounds, eg. triazole or imidazole, to give ketene O,N-acetals in virtually quantitative yield and with high stereoselectivity, without significant formation of ketene N,N-acetals.

To carry out the novel process in practice, for example stoichiometric amounts of the ketene O,O-acetal and the amine are initially taken, and the mixture is heated at the reaction temperature, while stirring thoroughly (two-phase systems are formed in some cases). The reaction temperature is from 100° to 250° C., preferably from 180° to 200° C. The increasing homogenization of the mixture and elimination of phenol permit the beginning of the reaction, and its course, to be monitored. Advantageously, samples are taken from the reaction mixture at particular intervals, and the course of the reaction is monitored by means of gas chromatography or HPLC.

The reaction is terminated as soon as starting material is no longer present. The mixture is usually worked up by extracting the eliminated phenol from the organic solution of the end product, using an aqueous basic extracting agent, eg. sodium hydroxide solution or potassium hydroxide solution, preferably in a concentration of from 5 to 30% by weight in water. Suitable organic solvents are aliphatic hydrocarbons, ethers or esters and aromatic hydrocarbons, eg. toluene or o, m or p-xylene. However, it is also possible to extract the end product as a quaternary ammonium salt from the organic phase, preferably using an aqueous solution of a strong inorganic acid, eg. hydrochloric acid, hydrobromic acid, sulfuric acid, nitric acid or perchloric acid. After neutralization of the acid, the free ketene O,N-acetal can be isolated from the aqueous phase.

EXAMPLE

Preparation of Z-1-(1,2,4-triazol-1-yl)-1-(2,4-dichlorophenoxy)-3,3-dimethylbut-1-ene 30.4 g (0.075 mole) of 1,1-bis-(2,4-dichlorophenoxy)-3,3-dimethylbut-1-ene were heated together with 5.2 g (0.075 mole) of triazole to 180°–185° C. As soon as the reaction mixture appeared to be homogeneous and had assumed a reddish brown coloration (after about 2–3 hours), the content of starting compound was determined by means of HPLC. When the desired degree of conversion had been reached, the reaction mixture was cooled and then taken up in 200 ml of a 1:1 mixture of hexane and ethyl acetate, the solution was washed 2 or 3 times with the same volume of 5% strength sodium hydroxide solution and dried with Na$_2$SO$_4$, and the solvent was distilled off under reduced pressure. 22.2 g of ketene O,N-acetal were obtained. Isomer purity: 85% of Z isomer, determined by means of $^1$H-NMR and HPLC.

The compounds below were prepared in a similar manner.

![structure: R1—CH=C(R3)(O-phenyl-R2)]

| No. | R$^1$ | R$^2$ | R$^3$ | Physical data: $^1$H—NMR, purity of the isomers, δ values in CDCl$_3$ |
|---|---|---|---|---|
| 1 | (CH$_3$)$_3$C— | 2,4-Cl$_2$ | 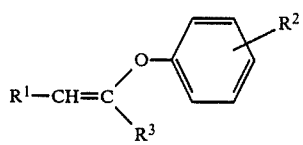 | 85% Z—Isomer δ = 1,25 (s, 9H), 5,85 (s, 1H), 6,7–7 (m, 3H) 7,85 (s, 1H), 8,1 (s, 1H) |

-continued

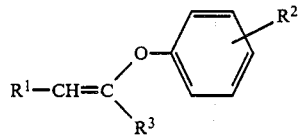

| No. | $R^1$ | $R^2$ | $R^3$ | Physical data: $^1H$—NMR, purity of the isomers, δ values in $CDCl_3$ |
|---|---|---|---|---|
| 2 | $(CH_3)_3C-$ | 4-Cl | (triazole) | 90% Z—Isomer<br>δ = 1,25 (s, 9H),<br>5,9 (s, 1H), 6,8–7,4 (m, 4H)<br>7,95 (s, 1H), 8,2 (s, 1H) |
| 3 | $(CH_3)_3C-$ | 2-Cl | (triazole) | 90% Z—Isomer<br>δ = 1,15 (s, 9H),<br>5,9 (s, 1H), 6,75–7,5 (m, 4H)<br>7,9 (s, 1H), 8,15 (s, 1H) |
| 4 | $(CH_3)_3C-$ | 4-Cl | (imidazole) | 80% E—Isomer<br>δ = 1,25 (s, 9H), 5,25 (s, 1H),<br>6,7–7,7 (m, 7H) |
| 5 | $(CH_3)_3C-$ | 2,4-$Cl_2$ | (imidazole) | 75% Z—Isomer<br>δ = 1,3 (s, 9H), 5,4 (s, 1H),<br>6,8–7,8 (m, 6H) |
| 6 | $(CH_3)_3C-$ | 2-Cl | (imidazole) | 80% Z—Isomer<br>δ = 1,25 (s, 9H),<br>5,35 (s, 1H), 6,7–7,8 (m, 7H) |
| 7 | $(CH_3)_3C-$ | 4-Cl | (benzimidazole) | 80% Z—Isomer<br>δ = 1,35 (s, 9H),<br>5,4 (s, 1H), 6,8–8,1 (m, 9H) |

We claim:
1. A process for the preparation of a predominantly E or Z isomer of a ketene O,N-acetal of the formula I

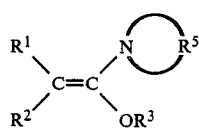

where $R^1$ is tertiary alkyl of 4 to 6 carbon atoms, $R^2$ is hydrogen, $R^3$ is phenyl which is unsubstituted or mono-, di- or tri-substituted with the same or different radicals selected from the group consisting of halogen, $C_1$–$C_2$-alkoxy, $C_1$–$C_4$-alkyl, phenyl, phenoxy, cyano, nitro and trifluoromethyl, and

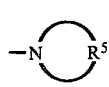

is a triazole or imidazole radical, wherein a ketene, O,O-acetal of the formula II

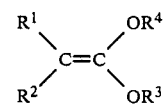

where $R^1$, $R^2$ and $R^3$ have the above meanings and $R^4$ is phenyl which is unsubstituted or substituted by halogen, $C_1$–$C_2$-alkoxy, $C_1$–$C_4$-alkyl, phenyl, phenoxy, cyano, nitro or trifluoromethyl, is reacted with a compound of the formula

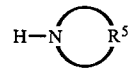

where

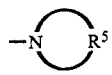
has the above meanings, at a temperature of from about 80 to 250 C.
2. The process of claim 1, wherein the reaction is carried out at from 100° to 250° C.
3. The process of claim 1, wherein
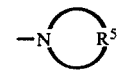
is a triazole radical.
4. The process of claim 1, wherein
is an imidazole radical.
* * * * *